United States Patent [19]

Isaacson

[11] Patent Number: 4,867,155
[45] Date of Patent: Sep. 19, 1989

[54] ARTHROSCOPIC CUTTING DEVICE

[75] Inventor: Milton S. Isaacson, Dayton, Ohio

[73] Assignee: Nu-Tech Industries, Inc., Dayton, Ohio

[21] Appl. No.: 209,427

[22] Filed: Jun. 21, 1988

[51] Int. Cl.⁴ ............................................. A61B 17/32
[52] U.S. Cl. .................................................. 128/305
[58] Field of Search ............... 128/304, 305, 355, 317; 604/22; 30/240, 263, 264, 276

[56] References Cited

U.S. PATENT DOCUMENTS

| | | |
|---|---|---|
| 3,214,869 | 11/1965 | Stryker. |
| 3,978,862 | 9/1976 | Morrison. |
| 4,036,236 | 7/1977 | Rhodes, Jr.. |
| 4,200,106 | 4/1980 | Douvas et al. ...................... 128/305 |
| 4,203,444 | 5/1980 | Bonnell et al.. |
| 4,217,964 | 8/1980 | Eaton. |
| 4,274,414 | 6/1981 | Johnson et al.. |
| 4,598,710 | 7/1986 | Kleinberg et al. .............. 128/305 X |
| 4,601,290 | 7/1986 | Effron et al. ......................... 128/305 |

OTHER PUBLICATIONS

Product Advertisement "The Stryker Microelectric Arthroplasty System #277-720: The Complete Powered System for Arthroscopic Hand Surgery" 5 pages, by Stryker Surgical.

Primary Examiner—Michael H. Thaler
Attorney, Agent, or Firm—Wood, Herron & Evans

[57] ABSTRACT

An arthroscopic cutting device has an external tube, a knife telescopically received within and rotatably mounted with respect to the external tube, a dc motor drivably connected to the knife and means for controlling the motor to periodically reverse the direction of rotation of the knife about every two revolutions, thus providing increased speed and efficiency in bidirectional cutting action during arthroscopic surgery.

2 Claims, 3 Drawing Sheets

ARTHROSCOPIC CUTTING DEVICE

FIELD OF THE INVENTION

This invention relates to an arthroscopic cutting device and more particularly to an arthroscopic cutting device that provides increased speed and efficiency in bidirectional cutting during arthroscopic surgery.

BACKGROUND OF THE INVENTION

The advent of arthroscopic surgery has revolutionized the field of joint surgery, most notably in the field of sports medicine with respect to surgery performed on the knee, perhaps the most vulnerable of human joints.

Generally, the word "arthroscope" refers to "viewing of the joint". Arthroscopic surgery involves the use of specialized tools which enable a surgeon to see the joint during surgery, without laying it open, as previously required. The ability to perform a surgical operation with very minimal intrusion into the joint reduces tissue trauma normally associated with surgical operations, thereby reducing previously required recovery and rehabilitation time.

Generally, to perform an arthroscopic surgery on a knee, for example, three surgical cuts are made. A tube is inserted into one of the cuts and saline solution is introduced into the joint through the tube. A tubular viewing scope is inserted into another one of these surgical cuts to allow a surgeon to actually view the joint. The viewing scope is often connected to a remote viewing screen to provide the surgeon with a better picture of the knee. Into the third of the surgical cuts is inserted a surgical cutting device to enable actual cutting of tissue that is to be removed from the joint. Initially, or for examination purposes, a surgical probe may be used, rather than a cutting device.

When arthroscopic cutting is required, it generally involves the removing of various types of tissue from the joint. This tissue can range from relatively soft synovial material which is attached to the walls of the joint to a relatively harder, gristle-like material, such as meniscal cartilage that may be found in the joint. An arthroscopic cutting device must be successful in shaving all of these types of tissue.

Because arthroscopic surgery entails only minimal intrusion into the joint through these three surgical cuts, the surgeon must perform within severely restricted space limitations. These space limitations often hinder access to the tissue to be cut and attempts to cut the tissue in an efficient manner.

Arthroscopic cutting devices have been designed with space limitations in mind. One typical arthroscopic cutting device has a housing designed to be hand held, an external tube projecting from the housing, a knife concentrically received within and rotatably mounted with respect to the external tube, a motor drivably connected to the knife and a motor controller. To provide cutting access for the rotatable knife, the external tube has a cutting port formed adjacent its free end. With respect to the external tube, the cutting port has circumferential and longitudinal dimensions so as to provide two opposing, oppositely directed, longitudinal edges. The longitudinal edges are adapted to cooperate with the rotating knife to shear tissue.

During arthroscopic cutting, the external tube is positioned within the surgical cut in order to project, in a relative manner, tissue through the cutting port. Rotation of the knife directs the tissue toward one of the longitudinal edges of the cutting port, where it is sheared between an edge and the rotating knife. Preferably, the rotatably mounted knife is tubular and in communication with a suction port formed in the housing. During cutting, suction is applied to the suction port to promote fluid flow of the saline. This draws tissue to be cut into the cutting port to facilitate shearing action and enable removal of discrete particles of tissue which have been cut.

One patent, U.S. Pat. No. 4,203,444, suggests that the knife provide two oppositely directed blades, each blade designed to cooperatively shear with one of the longitudinal edges of the cutting port during rotation in one direction. The motor is connected to the knife to provide bidirectional rotation of the knife. An initial direction of rotation may be selected, and subsequently reversed, to enable bidirectional cutting to take place. Bidirectional cutting enables the surgeon to remotely clean the instrument if it becomes jammed.

During bidirectional cutting, the location of shearing alternates between the two longitudinal edges, which results in faster cutting action. Otherwise, continuous rotation of the knife in the same direction eventually directs tissue beyond one longitudinal edge to a point where the blade no longer has cutting access. By reversing the direction of rotation of the knife, the tissue is directed back through the cutting port, toward the opposite longitudinal edge. While enroute to the opposite edge, the fluid flow pulls the tissue within the cutting port and the blade again has cutting access. A device which only rotates in one direction would have to be manipulated by the surgeon to produce the same effect. Such manipulation is undesirable from a practical standpoint.

The controller enables the surgeon to select a desired speed of rotation for the knife. U.S. Pat. No. 4,203,444, has cited advantageous cutting at speeds of rotation ranging from 100 rpm to 200 rpm.

Such bidirectional cutting requires a physical switching procedure to affect a reversal of the direction of rotation of the blade. Such a procedure, for example, might involve the simple flipping of a switch on the controller. Regardless, no matter how simple the procedure, the successive repetition of the same procedure is tedious and time consuming, and not desirable in an operating room environment.

Moreover, the reversal itself is also time consuming. The higher the speed of rotation of the motor, the greater the rotational inertia that must be overcome in order for rotation in one direction to stop, and rotation in the opposite direction to begin. Until this rotational inertia is overcome, the knife continues to rotate in the undesired direction. Meanwhile, the surgeon must wait for the reversal to occur before commencing arthroscopic cutting in the desired direction. In other words, if time is saved by cutting at higher speeds, that time is lost when the direction of rotation of the knife is reversed, and the surgeon must wait for reversal to take place.

Repetitive performance of the reversing procedure, coupled with the waiting period required for the motor to reverse itself, unnecessarily extend the duration of arthroscopic knee surgery. Additionally, the benefits of bidirectional cutting are limited by the tendency to cut at slower speeds, in order to reduce this waiting period.

It is therefore an objective of this invention to provide a bidirectional arthroscopic cutting device which does not require the performance of repetitive switching procedures in the operating room.

It is also an objective of this invention to provide a bidirectional arthroscopic cutting device having high speed cutting advantages without the disadvantages associated with waiting for reversal of rotation to occur.

It is a further objective of this invention to provide an arthroscopic cutting device which cuts with increased speed and efficiency.

SUMMARY OF THE INVENTION

To these ends, an improved arthroscopic cutting device has a rotatably mounted knife driven by a brushless dc motor, with means for controlling the motor which will automatically periodically reverse the direction of rotation of the knife about every two revolutions at a selectable speed of rotation ranging from about 75 rpm to about 2500 rpm. Thus, for instance, during one entire cycle of knife rotation, the knife rotates clockwise for about two revolutions, reverses direction, then rotates counterclockwise about two revolutions and again reverses direction.

Automatic reversal of the direction of rotation of the knife after about every two revolutions is provided by a brushless dc motor and a control network associated therewith of the type disclosed in U.S. Pat. No. 4,027,215, and expressly incorporated herein by reference in its entirety. The control network is programmed to periodically reverse the direction of the motor and the gear train which couples the motor to the knife. The gear ratio of the motor to the knife is about 14.58 to 1.0.

At each reversal, the motor is capable of changing from about 10,000 rpm in one direction to 10,000 rpm in the opposite direction, with the reversal occurring in approximately 25 milliseconds. When used for arthroscopic cutting, with selectable knife speeds of rotation ranging from about 75 rpm to about 2500 rpm, the direction of rotational cutting is capable of being reversed within about 25 to 75 milliseconds. The elapsed time during reversal depends upon the rotational speed of the motor. At higher speeds, it takes longer to reverse.

Although optimum cutting results have been obtained with knife speeds of about 300 r.p.m. (motor speed about 4374 r.p.m.) and 400 rpm (motor speed about 5832 r.p.m.) and reversal of the direction of knife rotation occurring approximately every 2.7 revolutions of the knife, the arthroscopic cutting device of this invention is capable of knife rotational speeds of up to 2500 rpm, with reversal about every two revolutions. Reversal within this time frame virtually eliminates the waiting period formerly associated with high speed, bidirectional cutting. Thus, a surgeon is able to uniformly cut meniscal cartilage or other types of tissue with increased speed and efficiency. Periodic reversal of the direction of rotation of the knife, in effect an oscillation, also provides automatic shearing action at both longitudinal edges of the cutting port without requiring the repetitive performance of a physical switching procedure.

By alternately shearing at one longitudinal edge, and then the other, about every two revolutions, in conjunction with saline flow into the cutting port, the rotating knife agitates the tissue with a high speed back and forth motion to continuously redirect it within the cutting port, rather than beyond it. This ensures that the rotating knife, via one of the blades, will have relatively constant cutting access to the tissue.

The present invention can be further appreciated in light of the following detailed description and the drawings in which:

DETAILED DESCRIPTION OF THE DRAWINGS

Figure 1:
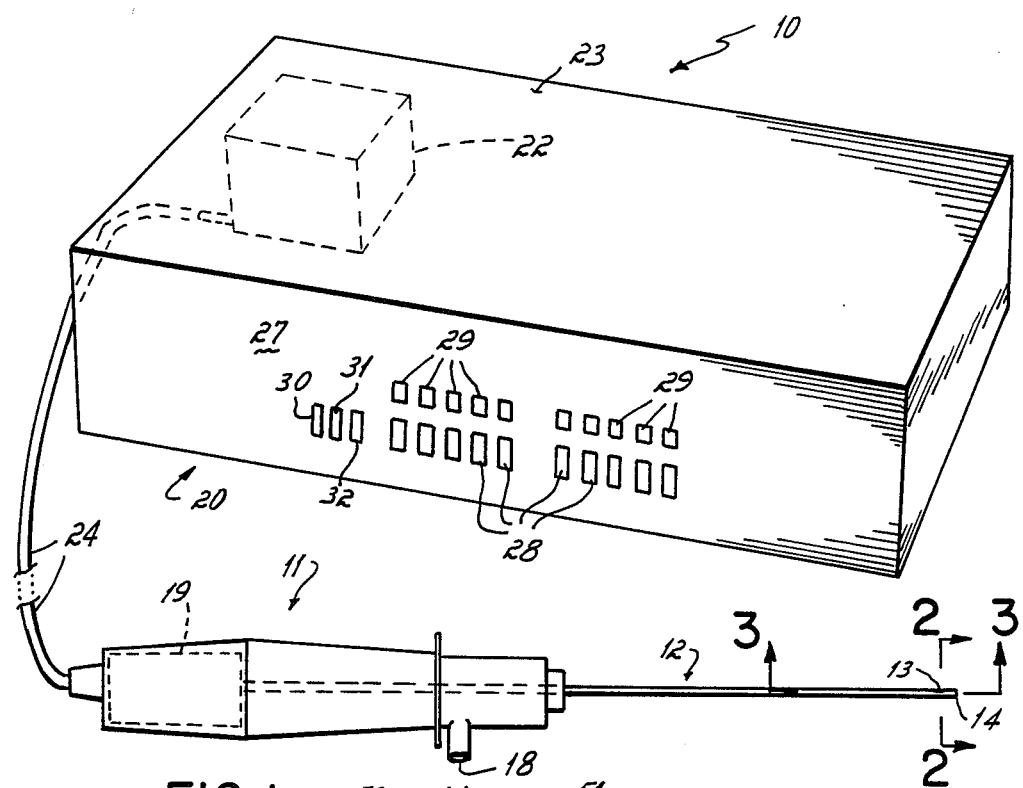
FIG. 1 is a plan view of the arthroscopic cutting device of this invention.

FIG. 1 shows an arthroscopic cutting device 10 of this invention. A tubular housing 11 is designed to be hand held by a surgeon during arthroscopic surgery. An external tube 12 is mounted to the housing and projects axially therefrom. The external tube 12 has a cutting port 13 formed adjacent a free end 14. The cutting port 13 provides cutting access for a knife 17 which is concentrically received within and rotatable with respect to the external tube 12. The rotating knife 17 is adapted to cooperate with an edge surface of cutting port 13 to provide shearing action of tissue which is projecting through the cutting port 13. Preferably, the knife 17 is tubular, and in communication with a suction port 18 formed in housing 11. During arthroscopic cutting, suction may be applied to suction port 18 to promote saline flow into the cutting port, thereby drawing tissue toward the cutting edges and facilitating removal of cut tissue particles from the joint.

Preferably, a dc brushless motor 19 and means for controlling 20 associated therewith are of the type disclosed in U.S. Pat. Nos. 4,027,215. U.S. Pat. No. 4,238,717, a continuation-in-part of U.S. Pat. No. 4,027,215, is also expressly incorporated herein by reference in its entirety. The motor 19 resides within housing 11 and is drivably connected to the knife 17. The motor 19 is lightweight and has dimensions no greater than approximately ¼ inch outside diameter and 1.75 inches long, to easily fit within the hand-held housing 11.

Means 20 for controlling the motor generally comprises a remotely located control circuit 22 mounted within a control housing 23 and connected to motor 19 via a cord 24. The cord 24 carries electrical conductors therein to convey electrical power and signals to and from the motor 19 to the control circuit 22. Preferably, the control housing 23 has a front panel 27 which displays a plurality of depressable pushbuttons 28, each having a speed designation 29 associated therewith to indicate a selectable speed of rotation for the knife 17. For the purposes of this invention, it is contemplated that the selectable speeds will range from about 75 revolutions per minute to about 2500 revolutions per minute. This allows the surgeon to select a relatively high cutting speed, and still obtain the benefits of bidirectional cutting.

Preferably, front panel 27 also presents pushbuttons/switches, 31 and 32, which enable selection of either continuous rotation, or oscillatory, i.e., periodic reversal, of the knife 17, respectively. Depression of a start/stop pushbutton 30 provides power to energize the control circuit 22 at a speed designated by the setting of a switch which is controlled by depressing one of the selectable speed pushbuttons/switches 28. Preferably, pushbuttons 31 and 32 differ in color from pushbutton 30, in order to enable an operator to visually distinguish between the mode pushbutton and the on/off pushbutton.

A power supply (not shown) for the motor 19 and the control circuit 22 may comprise any conventional power supply capable of generating an output signal having a voltage which is sufficient to power the connected motor 19 at the desired speed of rotation. The necessary voltage will vary according to the selected speed of operation. A 36 volt d.c. potential should be sufficient for the highest speeds contemplated for this invention. The power supply may be mounted within housing 23 or located remotely therefrom.

The improvements of this invention over prior arthroscopic cutting devices are obtained by combining a dc brushless motor and the control system associated therewith, of the type disclosed in U.S. Pat. No. 4,027,215, with a conventional bi-directional cutting device to provide high speed, automatic reversal of the knife.

The dc brushless motor 19 used in this invention includes a rotor member with means for producing a magnetic field therein fixedly oriented with respect to the rotor. The rotor is rotatably mounted within a stator which has a plurality of windings. Means are provided for applying periodic power pulses to the stator windings. When current passes through a stator winding, there is a torque due to the interaction of the winding generated flux and the rotor field, that causes the rotor to rotate. A power control system responds to signals induced in unpowered stator windings by the rotating rotor field to produce power pulses at a predetermined frequency. The pulse duration and amplitude are adjusted by the control system. These power pulses are applied to the stator windings in a predetermined sequence to produce a rotating flux which causes the machine to operate like a speed-controlled DC commutator motor at fixed selectable speeds for a wide range of motor torques.

Preferably, the control circuit 22 consists of a microprocessor, a pulse generator having an output fed into the microprocessor and an electronic power switch. A microprocessor commercially available as Motorola Catalog Number MC 68701 is suitable. The pulse generator is preferably a 555 timer. The time period between pulses from the pulse generator is adjusted to specific predetermined values by fixed resistor selection through activation of one of the pushbuttons 28 located on front panel 27. These predetermined time periods set the desired operating speed of the motor by becoming the real-time timing reference input to the microprocessor element.

The generated back EMF from the non-energized motor coil is converted from analog to digital information and input into the microprocessor. Within the microprocessor, the back EMF information is compared with the pulse generator input to determine the actual speed of the motor relative to the desired operating speed. This relationship and the digital back EMF code is interpreted by the software resident in the microprocessor to direct an output from the microprocessor to the electronic power switch in proper sequence, at the correct time and of the correct duration to provide a power flow to the motor coils that produce maximum torque and desired operating speed. An output is also directed to the internal power supply control element to provide to the motor the correct predetermined voltage level to achieve maximum motor efficiency. The microprocessor performs these comparisons, calculations and outputs for each motor coil every 180 electrical degrees, acting to maintain the desired operating speed under varying motor loading conditions.

Figure 4:
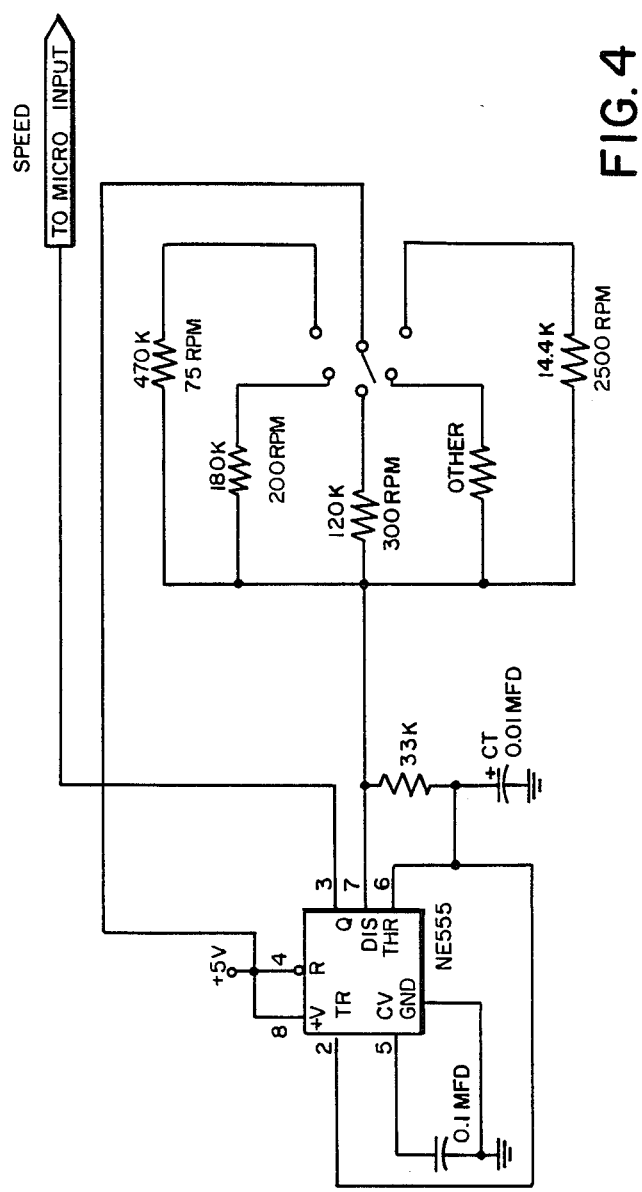
FIG. 4 is a schematic diagram showing a preferred embodiment of a motor speed pulse generator circuit of this invention.

As shown in FIG. 4, the motor speed pulse generator circuit preferably consists of a 555 timer I.C. connected to operate as a free running astable multivibrator. The frequency of operation is determined by the charge/discharge rate of timing capacitor, $C_T$ connected to pin 7. The discharge rate is set by the 33K ohms resistor connected between pin 6 and pin 7 which sets the time that the output signal remains low. The charge time of $C_T$ is determined by the sum of the 33K ohms resistor between pins 6 and 7 plus the resistor connected between pins 7 and 8 and selected by operation of switch 28 on the front panel.

In operation, the discharge (output low) time of $C_T$ is a constant duration pulse of about 230 uSec but the charge time is varied by changing the charging resistance value by Switch 28 selection. In the circuit illustrated selection of 200 RPM by switch 28 connects 180K ohms between pins 7 and 8 providing a charge time (output high) of about 1.50 mSec. When the 300 RPM selection is made by Switch 28, 120K ohms is connected resulting in a charge time (output high) of about 1.00 mSec. When considered in the frequency domain this change in charge times between the 200 RPM and 300 RPM speed selections is in direct proportion to the ratio of desired motor speeds. Likewise, other speeds can be set by proper selection of resistor values at Switch 28.

Because back EMF occurs only with rotor velocity, no back EMF code is available to the microprocessor at motor startup. To achieve starting, a specific sequence of pulses is provided to the electronic power switch from information contained in the microprocessor software. Once sufficient rotor velocity is achieved a back EMF code is detected at the microprocessor input and the microprocessor software begins the comparison and calculations as required to maintain desired operating speed.

Pushbuttons 31 and 32 on the front panel 27 are electrically connected to inputs of the microprocessor. The digital codes present at these inputs are translated by the microprocessor software to provide the correct sequence of outputs to the electronic power switches to achieve the desired operation. For instance, pushbutton 31 provides the sequence of outputs corresponding to continuous rotation, and pushbutton 32 provides the sequence of outputs necessary for oscillatory rotation. Analogizing to the discrete circuit of U.S. Pat. No. 4,027,215, where the position of a switch 51 determines the stepping switch sequency of the controller and hence the direction of rotation of the motor, for this arthroscopic cutting device, depressing of pushbutton 31 fixes stepping switch sequency to provide continuous rotation at a speed set by one of the pushbuttons 28. To select oscillatory operation, depression of pushbutton 32 actuates a programmable digital flip flop within the microprocessor to reverse the stepping switch sequency at a periodic predetermined rate to affect reversal of the knife 17.

Figure 5:
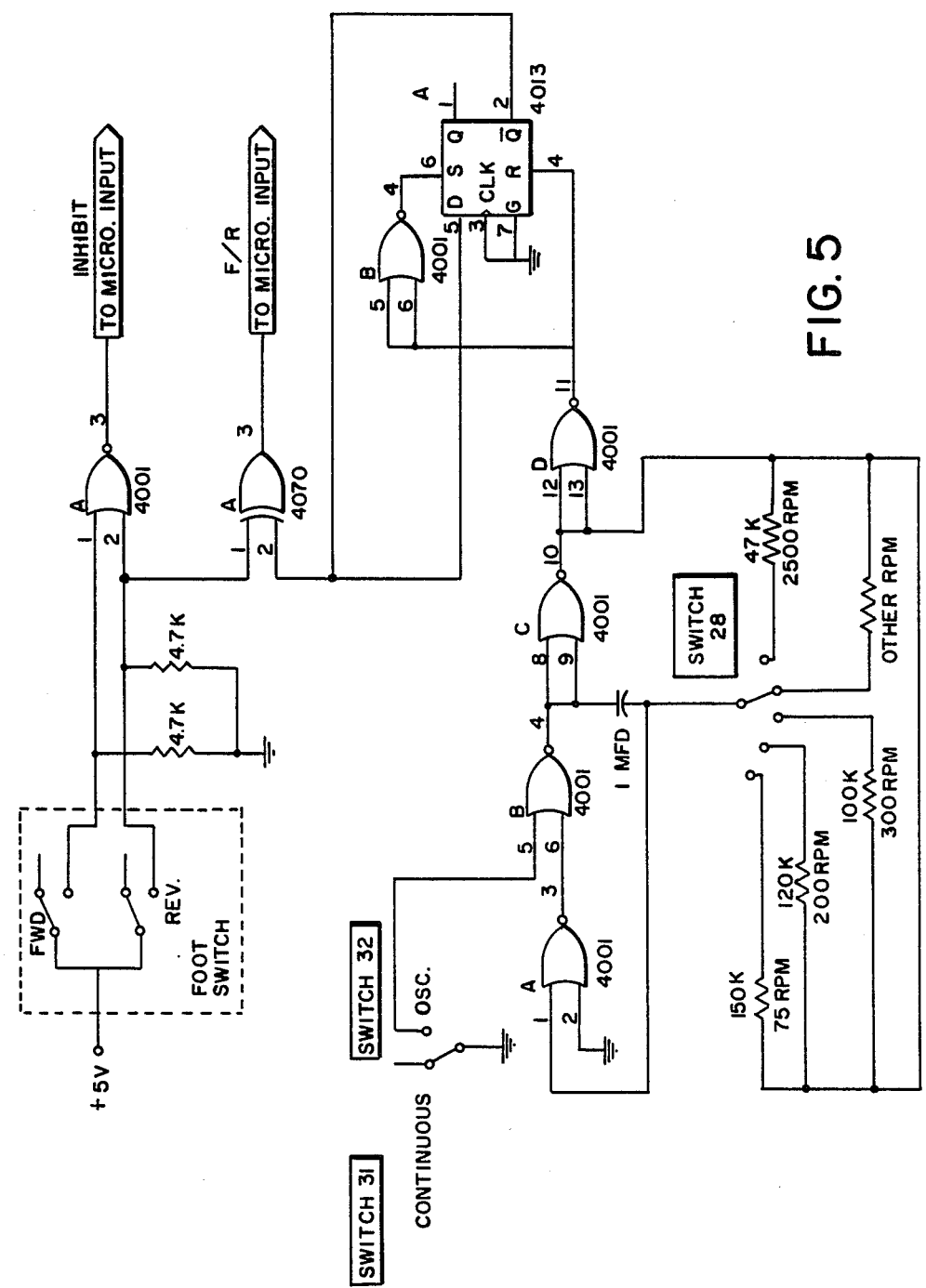
FIG. 5 is a schematic diagram of a preferred embodiment of an oscillating control circuit of this invention.

Oscillatory control can be provided by a circuit as shown in FIG. 5. Several 4001 NOR gates are connected to form a multivibrator circuit whose period is determined by the resistor value selected by one of the pushbuttons 28, a 4013 D-Q flip-flop for signal conditioning and outputting to an input of a 4070 Exclusive OR gate, that can be made part of a pedal control circuit, (also shown in FIG. 5) plus Switch 32 on the front panel for selection of continuous or oscillatory knife rotation. When pushbutton 31 is depressed the multivibrator circuit becomes inoperative and a "0" is outputted from the flip-flop to the Exclusive OR gate, and the knife rotates continuously.

When pushbutton 32 is depressed, the 1 microfarad capacitor is allowed to alternately charge and discharge through the selected series resistor which results in an alternating (1 to 0 to 1, etc.) and inverted signal being provided to the R and S inputs, respectively, of the 4013 flip-flop. These alternating inputs result in an alternating output from the 4070 Exclusive OR gate to the microcomputer input, with each alternating input to the microcomputer changing the direction of rotation of the motor.

Alternately, oscillatory operation can be achieved by software in the microcomputer. This would involve the counting of motor pulses outputted to the power switches by the program. With proper inputs to the microcomputer to indicate which speed has been selected by Switch 28, a different number of knife revolutions in each direction of rotation could be incorporated.

Note that depressing pushbutton 28 will set a resistance value according to the desired speed of rotation of the knife, according to the circuit shown in FIG. 4. Pushbutton 28 will also set another resistance value corresponding to the desired time interval between reversals in the direction of rotation of the knife, as shown in FIG. 5.

It has been found that optimum cutting is provided when the fixed resistor values are set to provide a cycle period of about 1.7 seconds. When the knife rotates at about 300 revolutions per minute, or at about 400 revolutions per minute, this results in knife rotation per half cycle of about 2.7 and about 3.7, respectively.

Figure 2:
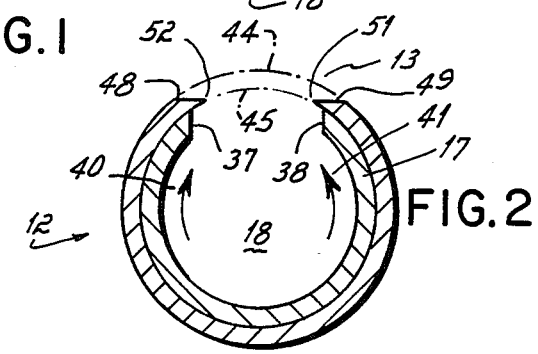
FIG. 2 is a transverse cross-sectional view taken along lines 2—2 of FIG. 1.
Figure 3:
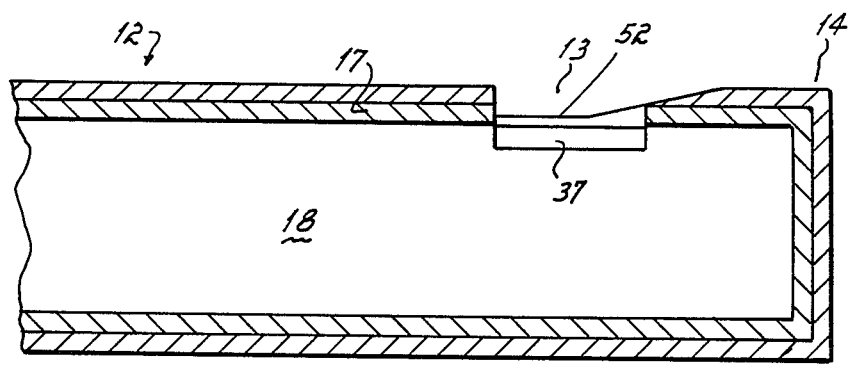
FIG. 3 is a longitudinal cross-sectional view taken along lines 3—3 of FIG. 1.

FIG. 2 shows how cutting advantages are provided by periodic reversal of the stepping switch sequency. The rotatably mounted knife 17 has oppositely directed cutting blades 37 and 38 to provide beneficial cutting action during rotation of the knife 17 in the direction shown by directional arrows 40 and 41, respectively.

The blades 37 and 38 cooperate with the cutting port 13 to shear cartilage projected therethrough. The cutting port 13 is generally defined or outlined by outside phantom arc 44 and inside phantom arc 45, which terminate at oppositely directed longitudinal edges 48 and 49. During rotation of knife 17 in a clockwise direction, indicated by directional arrow 40, blade 37 cooperates with longitudinal edge 49 to shear tissue which resides radially within inside arc 45. The shearing of tissue actually occurs along an edge or line 51 where longitudinal edge 49 and arc 45 meet. Similarly, during rotation of knife 17 in a counterclockwise direction, indicated by directional arrow 41, cutting blade 38 cooperates with longitudinal edge 48 to shear tissue residing along a line 52 where longitudinal edge 48 and arc 45 meet.

To perform arthroscopic cutting according to this invention, the housing 11 is manipulated by the surgeon to maneuver external tube 12 into the designated surgical cut. A viewing scope is positioned within another one of the surgical cuts to enable viewing of the joint, and a saline tube is inserted into the third of the cuts. The surgeon can direct, in a relative manner, the external tube 12 to position tissue to be cut within cutting port 13. Preferably, if the relative positions of the rotatable knife 17 and the cutting port 13 permit, the tissue can be projected across inside arc 45 to reside within the path of one of the blades, 37 or 38, to ensure immediate cutting action upon rotation of the knife 17. Saline flow also acts upon the tissue to pull it within the opening 13. By depressing a selectable speed pushbutton 28, the on/off pushbutton 30 and pushbutton 32 (oscillatory mode), the control circuit 22 is energized to start up the motor 19 and impart rotational movement to the knife 17, with automatic reversal of the direction of rotation occurring about every two revolutions. Alternatively, selection of pushbutton 31 instead of pushbutton 32 energizes the motor 19 to impart continuous rotational movement to the knife 17.

Because faster and more uniform cutting action is achieved by attacking the cartilage from opposite sides, it is desirable to alternately shear at opposite longitudinal edges 48 and 49. By programming the control circuit 22 to periodically reverse the direction of rotation of knife 17 within about every two revolutions, the location of the shearing action alternates between the opposing longitudinal edges, 48 and 49, at a rate that could not possibly be matched by former such devices, which required physically reversing the motor to affect bidirectional cutting. Thus, with the arthroscopic cutting device 10 of this invention, the time required to perform uniform arthroscopic cutting is significantly reduced.

Another inherent advantage of high speed periodic reversal is caused by continuous agitation of tissue during fluid flow into the cutting port 13. During cutting by a rotating blade, initially the tissue will be forcibly directed tangential to the direction of rotation. Eventually, the tissue will be either sheared between a blade and an edge or forcibly directed past the shear line (either shear line 51 or shear line 52 depending upon the direction of rotation). Unless the external tube 12 is physically moved to direct this tissue back within cutting port 13, it will remain out of the path of the rotating knife until a reversal takes place. Reversal will forcibly direct the tissue back through the cutting port 13 and eventually past the opposite shear point.

The arthroscopic cutting device 10 of this invention provides advantages due to utilization of high frequency reversal. High frequency reversal, about every two revolutions of the knife, agitates the tissue, and along with fluid flow through the cutting port 13, directs the tissue toward the cutting blades. When reversal occurs at such a high frequency, less time elapses with the tissue residing past a shear point, beyond the access of the knife 17. Although tissue is still forcibly directed by the rotation of the knife 17, it spends a greater proportion of its time within arc 45, thus providing proportionately more time for cutting access for the rotating blades. In short, the high frequency agitation of this invention maximizes the exposure of the tissue to the rotating cutting blades, thus providing faster, more efficient, cutting action.

While the above description constitutes a preferred embodiment of the arthroscopic cutting device of this invention, it is to be understood that the invention is not limited thereby and that in light of the present disclosure of the invention, various other alternative embodiments will be apparent to a person skilled in the art. Accordingly, it is to be understood that changes may be made without departing from the scope of the invention as particularly set and claimed.

We claim:

1. An arthroscopic cutting device comprising:
   an external tube;
   a knife concentrically received within said external tube and rotatably mounted with respect thereto;
   a motor drivably connected to said knife; and
   means for controlling said motor to enable the selection of either oscillatory or continuous rotation of said knife, said oscillatory rotation providing automatic periodic reversal of the direction of rotation of said knife about every two revolutions at speeds ranging from about 75 revolutions per minute to about 2500 revolutions per minute.

2. An arthroscopic cutting device comprising:
   an external tube having a free end, said tube having an opening adjacent said free end presenting two opposed cutting edges;
   a knife rotatably mounted within said external tube and presenting two cutting blades, each said cutting blade adapted to cooperate with a respective cutting edge in said external tube;
   a motor drivably connected to said knife; and
   means for controlling said motor to enable the selection of either oscillatory or continuous rotation of said knife, said oscillatory rotation causing said knife to automatically reverse the direction of rotation after a predetermined number of revolutions at speeds up to 2500 revolutions per minute.

* * * * *

UNITED STATES PATENT AND TRADEMARK OFFICE
CERTIFICATE OF CORRECTION

PATENT NO. : 4,867,155
DATED : September 19, 1989
INVENTOR(S) : Milton S. Issacson It is certified that error appears in the above-identified patent and that said Letters Patent is hereby corrected as shown below:

Column 4, line 48, delete "¼ inch" and insert -- 3/4 inch --

Signed and Sealed this

Thirteenth Day of November, 1990

Attest:

HARRY F. MANBECK, JR.

*Attesting Officer*   *Commissioner of Patents and Trademarks*